US010238331B2

(12) United States Patent
Jedwab et al.

(10) Patent No.: US 10,238,331 B2
(45) Date of Patent: Mar. 26, 2019

(54) APPARATUSES AND METHODS FOR DIAGNOSING SWALLOWING DYSFUNCTION

(75) Inventors: Michael Reuben Jedwab, Lausanne (CH); Adam Stewart Burbidge, Arzier (CH); Jan Enghmann, Epalinges (CH); Andreas Henning Busch, Lausanne (CH)

(73) Assignee: Nestec S.A., Vevey (CH)

( * ) Notice: Subject to any disclaimer, the term of this patent is extended or adjusted under 35 U.S.C. 154(b) by 770 days.

(21) Appl. No.: 13/982,169

(22) PCT Filed: Jan. 27, 2012

(86) PCT No.: PCT/IB2012/000218
§ 371 (c)(1),
(2), (4) Date: Jul. 26, 2013

(87) PCT Pub. No.: WO2012/101514
PCT Pub. Date: Aug. 2, 2012

(65) Prior Publication Data
US 2013/0310661 A1    Nov. 21, 2013

Related U.S. Application Data

(60) Provisional application No. 61/437,051, filed on Jan. 28, 2011.

(51) Int. Cl.
*A61B 5/00* (2006.01)
*A61B 5/11* (2006.01)
(52) U.S. Cl.
CPC .......... *A61B 5/4205* (2013.01); *A61B 5/1107* (2013.01); *A61B 5/6822* (2013.01);
(Continued)

(58) Field of Classification Search
None
See application file for complete search history.

(56) References Cited

U.S. PATENT DOCUMENTS

| 8,696,568 | B2 * | 4/2014 | Jedwab | A61B 5/00 600/300 |
| 9,138,171 | B2 * | 9/2015 | Chau | A61B 5/11 |

(Continued)

FOREIGN PATENT DOCUMENTS

| EP | 1453088 | | 9/2004 | |
| JP | 2005304890 | A * | 11/2005 | |
| WO | WO 2008157298 | A2 * | 12/2008 | G01D 11/245 |

OTHER PUBLICATIONS

Berggren et al, Organic materials for printed electronics, Nature Materials, vol. 6, pp. 3-5, (2007).*

(Continued)

*Primary Examiner* — Christopher A Flory
*Assistant Examiner* — Qingjun Kong
(74) *Attorney, Agent, or Firm* — K&L Gates LLP

(57) ABSTRACT

The present disclosure is directed to apparatuses and methods for diagnosing a swallowing dysfunction. The apparatuses may include a multi-parametric dysphagia analysis system in a plastic foil. The analysis systems may be smart sensing systems that are flexible, lightweight, and based on substrates having low-cost printed electronics technologies thereon. The methods may include measurement and classification of non-invasive parameters that may be indicative of a swallowing dysfunction or the probability of same. In a general embodiment, the methods include placing a sensor on a patient for measurement of at least one parameter associated with the patient's swallowing profile. The measured parameter is then analyzed and compared with several known normal and dysphagic swallowing profiles to provide (Continued)

an indication of the probability of an underlying swallowing dysfunction.

5 Claims, 2 Drawing Sheets

(52) U.S. Cl.
CPC .......... *A61B 5/6832* (2013.01); *A61B 5/7275* (2013.01); *A61B 2503/40* (2013.01); *A61B 2562/0204* (2013.01); *A61B 2562/0219* (2013.01); *A61B 2562/0247* (2013.01); *A61B 2562/164* (2013.01); *A61B 2562/166* (2013.01)

(56) References Cited

U.S. PATENT DOCUMENTS

| | | | | |
|---|---|---|---|---|
| 2008/0269646 | A1* | 10/2008 | Chau | A61B 5/11 600/595 |
| 2009/0118594 | A1* | 5/2009 | Zdeblick | A61B 5/117 600/300 |
| 2009/0125333 | A1* | 5/2009 | Heywood | A61B 5/0002 705/3 |
| 2009/0227908 | A1 | 9/2009 | Chau et al. | |
| 2010/0160833 | A1 | 6/2010 | Chau et al. | |
| 2010/0245114 | A1 | 9/2010 | Celik-Butler et al. | |
| 2012/0209089 | A1* | 8/2012 | Garde | A61B 5/103 600/301 |

OTHER PUBLICATIONS

Allen et al, Prevalence of penetration and aspiration on videofluoroscopy in normal individuals without dysphagia, Otolaryngol Head Neck Surg, Feb. 2010, vol. 142, No. 2, pp. 208-213.*

Joon et al, A radial basis classifier for the automatic detection of aspiration in children with dysphagia, Journal of NeuroEngineering and Rehabilitation, 2006, 3:14.*

"ADXL322—Small and Thin ±2 g Accelerometer," Analog Devices, Rev. 0, Catalog, Undated, pp. 1-16. XP002680614.

Japan Office Action for Application No. P2013-550964, Dispatch No. 002819, dated Jan. 5, 2016, 7 pages.

* cited by examiner

APPARATUSES AND METHODS FOR DIAGNOSING SWALLOWING DYSFUNCTION

CROSS REFERENCE TO RELATED APPLICATIONS

The present application is a National Stage of International Application No. PCT/IB2012/000218, filed on Jan. 27, 2012, which claims priority to U.S. Provisional Patent Application No. 61/437,051, filed Jan. 28, 2011, the entire contents of which are being incorporated herein by reference.

BACKGROUND

The present disclosure generally relates to health and nutrition. More specifically, the present disclosure relates to the diagnosis of a swallowing dysfunction based on the analysis of a number of swallowing-related parameters that may be indicative of same.

Dysphagia is the medical term for the symptom of difficulty in swallowing and refers to any deglutition (swallowing) disorder, which may include, for example, abnormalities within the oral, pharyngeal and esophageal phases of swallowing. Many complications can occur as a result of swallowing dysfunctions including, for example, dehydration, malnutrition, airway obstruction, dysfunctional immune response, etc. As a result, it is not only critical to detect and diagnose dysphagia and aspiration, but it is important to detect these conditions as early as possible. Unfortunately, it is estimated that approximately 80% of patients with dysphagia remain undiagnosed, which is thought to be due, at least in part, to the fact that general practitioners and nursing homes are relatively ill-equipped to diagnose these conditions. While several diagnostic tools exist for diagnosing dysphagia and aspiration, many of these tools are expensive, time-consuming, invasive, are only available in specialist centers, and may expose the patient to ionizing radiation.

Therefore, it would be beneficial to provide apparatuses and methods for diagnosing a swallowing dysfunction that are convenient, easy to use, cost-effective, provide rapid results and are widely available.

SUMMARY

The present disclosure provides devices for diagnosing a swallowing disorder or dysfunction. The devices include, for example, a flexible substrate with printed electronics selected from the group consisting of a microcontroller, at least one printed sensor, an antenna, or combinations thereof. The flexible substrate and printed electronics may be encased in a plastic foil.

In an embodiment, the flexible substrate comprises a flexible polymer. The flexible polymer may be selected from the group consisting of polyethylene napthalate ("PET"), polyethylene terephthalate ("PET"), or combinations thereof. The sensor may be disposable.

In an embodiment, the printed electronics of the sensor include a plurality of printed sensors. The sensors may be configured to sense sound, acoustic, acceleration, velocity, distance, electromyography, mechanical myography, electrical, videofluouroscopy, thermography, temperature, or combinations thereof. The antenna may be configured to receive and/or transmit data.

In an embodiment, the sensor further includes an adhesive. The adhesive should be safe for use on skin and is easily removable therefrom.

In another embodiment, a method of diagnosing a disorder is provided. The method includes placing a sensor on a patient to be evaluated, the sensor communicating with a device that accepts a sensor output; evaluating the sensor output to obtain a first result; and outputting the first result of the evaluation. The method may further include evaluating the first result to obtain a second result; and outputting the second result. The first and second results may be output to a display.

In an embodiment, the sensor communicates via wiring, or via a wireless connection. The connection may also occur via Bluetooth, radiowaves, or a cellular telephone network.

In an embodiment, the evaluating occurs at a patient database. The patient database may be in the same building as the patient. The evaluating may occur within 10 minutes of the sensor communicating with the device, or substantially instantaneously. The evaluating may occur in a cost-effective, validated, sensitive, specific and reliable manner. The evaluating may also occur without clinician-specific variability, and in a simplified manner for non-specialists' use. The evaluating can include comparing the sensor output to known disorders/dysfunctions in a patient database. In an embodiment, the evaluating uses an algorithm to interpret the sensor output.

The patient database can be updated. The database can be updated by entering a result of a new test into the database. The patient database may update by subscription. The patient database updates may be received by at least one of internet, physical means, and the internet and physical means. The physical means can be at least one of a compact disc, a DVD, a flash drive, tape, other physical data storage devices, or combinations thereof. The patient database may contain statistically-significant data. The patient database may contain about 5000 test results, and may be used by a plurality of patient testing sites.

In an embodiment, the evaluating occurs at a central database. The central database is capable of being updated and may update by subscription. The central database updates may be received by at least one of internet, physical means, and the internet and physical means. The physical means can be at least one of a compact disc, a DVD, a flash drive, tape, other physical data storage devices, or combinations thereof. The central database may contain statistically-significant data. The central database may contain about 5000 test results, and may be used by a plurality of patient testing sites.

In an embodiment, the central database may be configured to gathers data from a user site. The central database may be configured to gather data to learn, wherein the learning comprises normal variants, or a composite normal. The central database may be configured to gather data to advance science and to continuously improve the evaluating. The central database may be located in a hospital or a specialty-clinic.

In an embodiment, the further evaluating is comparing evaluation output to known treatments and/or standard interventions. The further evaluating may include using an algorithm to interpret the second output and determined one or more appropriate treatments. The further evaluating can occur at a patient database. The patient database may have the same characteristics as the patient database described above.

In an embodiment, the evaluating the first result to obtain a second result occurs at central database. The first and/or second results may be visual, audible, Braille, at least one electronic signal, a diagnosis of a disorder or a dysfunction, at least one qualitative measure of the disorder or the dysfunction, at least one quantitative measure of the disorder or the dysfunction, "does the patient have a disorder/dysfunction"?, mechanical dysfunction, at least one qualitative measure of the mechanical dysfunction, at least one quantitative measure of the mechanical dysfunction, biomechanical dysfunction, at least one qualitative measure of the biomechanical dysfunction, at least one quantitative measure of the biomechanical dysfunction, neurologic dysfunction, at least one qualitative measure of the neurologic dysfunction, at least one quantitative measure of the neurologic dysfunction, a qualitative measure of dysphagia, swallowing impairment, poor swallow, safety and/or efficacy, a quantitative measure of dysphagia, swallowing impairment, poor swallow, safety and/or efficacy, a classification of swallowing dysfunction, at least one qualitative measure of the dysfunction, at least one quantitative measure of the dysfunction, a classification of a disorder, at least one qualitative measure of the disorder, at least one quantitative measure of the disorder, a classification of a dysphagia type, a diagnosis of anatomic structures not functioning within normal parameters, a quantitative measure of various parameters of one or more functions of one or more anatomical structure, a quantitative measure of various parameters of one or more functions of one or more anatomical structure, a risk of sequellae from a disorder.

In an embodiment, the sequellae is selected from the group consisting of aspiration pneumonia, chronic obstructive pulmonary disorder ("COPD"), malnutrition, sarcopenia, dehydration, orthostatic hypotension, functional decline, falls, pressure ulcers, urinary tract infections, skin infection, conditions of specific nutrient deficiencies, choking, coughing, anxiety, depression, or combinations thereof. The sequellae may require emergency care or at least one of a hospitalization visit, a doctor's office visit, medical treatment, or medication. The sequellae may be dehydration and associated problems and healthcare burdens.

In an embodiment, the disorder is dysphagia. The first and/or second results may be a risk of aspiration pneumonia from dysphagia.

In an embodiment, the sensor device is in a location remote from a patient database. In an embodiment, the remote location is at least one of a care giver's office, a skilled nursing facility, and a long-term care facility. The care giver's office may be a physician's office, a hospital, a clinic. The remote location may also be a mobile location. The mobile location may be a home health care provider. The mobile location may also be a clinic on wheels or a flying care unit.

In an embodiment, an evaluation outputs a result that includes a recommended therapy. The recommended therapy may be at least one of products, tools and services tailored for the patient based on a disease or dysfunction of the patient. The recommended therapy may be a therapy plan including at least two of: physical therapy, occupational therapy, speech therapy, nutritional formulation, dietary modification, oral health improvement, electrical stimulation, biofeedback, and pharmacological treatment. Dietary modification can include at least one of: increased cohesiveness, increased thickness, trigeminal stimulants, swallowing stimulants, temperature modification of the food, texture modification of the food, and sensory modification of the food. Oral health improvement can include the use of at least one of mouth wash, toothpaste, probiotics, saliva stimulants, toothbrush, dental floss, and tongue scraping.

In an embodiment, the first result is a disorder selected from the group consisting of any pathologies, syndromes, diseases that can be diagnosed or classified using this disorder, or combinations thereof. The first result may be a disorder that is at least one arthropathy, temporal mandibular dysfunction, colic, irritable bowel syndrome ("IBS"), irritable bowel disorder ("IBD"), at least one intestinal disorder, a disorder that is at least one pathology, syndrome or disease that can manifest dysphagia.

In an embodiment, the methods include diagnosing a disorder or dysfunction. The diagnosis can be made at an early stage of the disorder or dysfunction. The methods may further include treating the patient at the early stage with respect to the disorder or dysfunction. As a result of diagnosing and treating the patient at the early stage reduces at least one of health costs, emergency room visits, hospitalizations, doctors visits, or medical treatments.

In an embodiment, reduced health costs are due to reduced sequellae from the disorder or dysfunction. The sequellae may be selected from the group consisting of aspiration pneumonia, chronic obstructive pulmonary disorder ("COPD"), malnutrition, sarcopenia, dehydration, orthostatic hypotension, functional decline, falls, pressure ulcers, urinary tract infections, skin infection, conditions of specific nutrient deficiencies, choking, coughing, anxiety, depression, or combinations thereof.

In an embodiment, the reduced health costs are due to reduced need for at least one of health care, medical treatment, and institutionalization.

In an embodiment, the reduced health costs are due to at least one of slowing of the progression of the disorder/dysfunction, optimizing quality of life, reducing depression, reducing pain, and reducing anxiety.

In an embodiment, the diagnosing and treating the patient at the early stage leads to reduced risk of at least one of malnutrition, dehydration, and associated problems. Diagnosing and treating the patient at the early stage can lead to early treatment of malnutrition, which can strengthen the immune system of the patient, lead to decreased occurrence of sarcopenia and associated problems, lead to decreased occurrence of dystonia of the muscles, and lead to decreased symptoms of the disorder or dysfunction.

In yet another embodiment, methods for reducing healthcare spending costs are provided. The methods include placing a sensor on a patient, gathering data relating to a swallowing profile of the patient using the sensor, comparing a sensor output to a database containing a plurality of swallowing profiles, diagnosing a swallowing dysfunction, and treating the swallowing dysfunctions or symptoms thereof. The reduction in healthcare spending costs can be due to decreased length of stay in a hospital, decreased length of stay in a healthcare facility, decreased complications or symptoms associated with the swallowing dysfunction, and decreased occurrences of patient visits to a healthcare center selected from the group consisting of a hospital, a clinic, a physician's office, or combinations thereof. The reduction in healthcare spending costs can also be due to an early diagnosis of the swallowing dysfunction and an early treatment of the swallowing dysfunction.

Early treatment of a swallowing dysfunction can include a therapy plan including at least one of products, tools and services known to be effective in treating the swallowing dysfunction. The early treatment can also include a therapy plan including at least two of physical therapy, occupational therapy, speech therapy, nutritional formulation, dietary modification, oral health improvement, electrical stimulations, biofeedback and pharmacological treatment. Dietary modification may include at least one of increased cohesiveness, increased thickness, trigeminal stimulants, swallowing stimulants, temperature modification of the food, texture modification of the food, and sensory modification of the food. Oral health improvement can include at least one of mouth wash, toothpaste, probiotics, saliva stimulants, toothbrush, dental floss, and tongue scraping.

In an embodiment, the reduction in healthcare spending costs is due to reduced sequellae from dysphagia. The sequellae can be selected from the group consisting of aspiration pneumonia, chronic obstructive pulmonary disorder ("COPD"), malnutrition, sarcopenia, dehydration, orthostatic hypotension, functional decline, falls, pressure ulcers, urinary tract infections, skin infection, conditions of specific nutrient deficiencies, choking, coughing, anxiety, depression, or combinations thereof.

In an embodiment, the reduction in healthcare spending costs is due to at least one of slowing of the progression of the dysfunction, optimizing the quality of life, reducing depression, reducing pain and reducing anxiety.

In still yet another embodiment, methods of diagnosing a dysfunction are provided. The methods include placing a sensor on a patient; measuring a level of function of an anatomical structure involved in swallowing, the sensor communicating with a device that accepts a sensor output representative of the level of function, evaluating the sensor output to obtain a result; and outputting the result of the evaluation.

In an embodiment, the sensor may have a flexible substrate, printed electronics, an antenna and a microprocessor. The sensor may be a known sensing device selected from the group consisting of videofluoroscopy, electromyography, mechanical myography, thermography, or combinations thereof.

In an embodiment, the anatomical structure is selected from the group consisting of a jaw, lips, a soft palate, a tongue, a hyoid, an epiglottis, a larynx, a pharynx, an upper esophageal sphincter, or combinations thereof.

In an embodiment, the level of function is selected from the group consisting of low, normal, high or combinations thereof. The level of function may also be selected from the group consisting of poor, normal, excellent or combinations thereof. The level of function may relate to at least one of lip closure, jaw closure, anchoring of the tongue, tongue lift, tongue control, tongue sweep, tongue seal, soft palate seal, mouth breathing, nasal breathing, lingual propulsion, tongue pressure, laryngeal elevation, hyoid movement, hyolaryngeal excursion, upper esophageal sphincter opening, epiglottis movement, larynx opening, vocal fold closure, laryngeal sensation, pharyngeal contraction, pharyngeal fatigue, laryngeal adductor reflex, laryngeal fatigue, respiration halting, respiration recommencement, and pharyngeal sensation.

In an embodiment, the device is a an electronic device having a processor. The electronic device may be selected from the group consisting of a computer, iPod, an iPhone, an iPad, a cell phone, a personal digital assistant ("PDA"), a pager, a short message service ("SMS") system, a Blackberry, or combinations thereof.

In an embodiment, the evaluating includes comparing the sensor output to a database containing a plurality of swallowing profiles. The plurality of swallowing profiles may include both healthy patient swallowing profiles and dysphagic patient swallowing profiles. The plurality of swallowing profiles comprises a statistically-significant amount of data.

In an embodiment, the result is output in a form that is easily understood by the patient. The output result can be in a form selected from the group consisting of visible, audible, textural, and combinations thereof. For example, the output result is visible and is selected from the group consisting of a print-out, an electronic display, a blinking light emitting diode ("LED"), a color-coded LED, or combinations thereof. The output result may also be Braille. The output result may be audible and is output from a speaker.

In another embodiment, a method of treating a swallowing dysfunction is provided. The method includes measuring a swallowing profile of a patient using a sensor, sending a sensor output to a device having a processor and a swallowing profile database, comparing the sensor output with the swallowing profile database to obtain a first result, comparing the first result to a recommended therapy database to obtain a second result, and treating the patient in accordance with the second result.

In an embodiment, the comparing is accomplished using the processor of the device.

In an embodiment, the first result is indicative of a swallowing dysfunction. The first result may be an electronic signal.

In an embodiment, the recommended therapy database is in the same device as the swallowing profile database.

In an embodiment, the method further includes sending the first result to a second device.

In an embodiment, the second result is a recommended therapy.

In an embodiment, the sensor includes a flexible substrate, printed electronics, an antenna and a microprocessor. The sensor may also include a known sensing device selected from the group consisting of videofluoroscopy, electromyography, mechanical myography, thermography, or combinations thereof.

In an embodiment, the device is selected from the group consisting of a computer, iPod, an iPhone, an iPad, a cell phone, a personal digital assistant ("PDA"), a pager, a short message service ("SMS") system, a Blackberry, or combinations thereof.

In an embodiment, the swallowing profile database includes both healthy patient swallowing profiles and dysphagic patient swallowing profiles. The swallowing profile database may further include a statistically-significant amount of data.

In an embodiment, the results are output in a form that is easily understood by the patient. The results may be output in a form selected from the group consisting of visible, audible, textural, and combinations thereof. The results may also be output in a visible form and are selected from the group consisting of a print-out, an electronic display, a blinking light emitting diode ("LED"), a color-coded LED, and combinations thereof. The output results may be Braille. The output results may be an audible signal output from a speaker.

Additional features and advantages are described herein, and will be apparent from the following Detailed Description and the figures.

DETAILED DESCRIPTION

Figure 1:
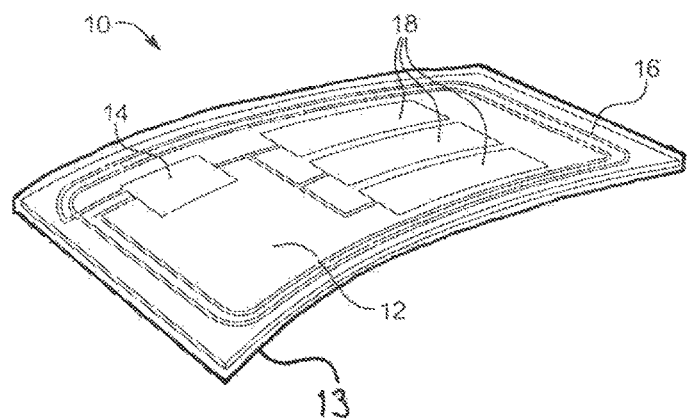
FIG. 1 illustrates a sensor device in accordance with an embodiment of the present disclosure.

The present disclosure is directed to apparatuses and methods for diagnosing a swallowing dysfunction by measuring and classifying of non-invasive parameters associated with a patient's swallowing profile that may be indicative of the probability of an underlying swallowing dysfunction. The apparatuses include, for example, a multi-parametric dysphagia analysis system in a plastic foil. The analysis system may be a smart sensing system that is a flexible, lightweight sensor that is based on a polymer substrate having low-cost printed electronics technologies thereon. In another embodiment, the sensor is a known sensing device such as, for example, a videofluouroscope ("VF"). The methods may include placing a sensor on a patient for measurement of at least one parameter associated with swallowing. The measured parameters are evaluated and compared to known swallowing dysfunction data and the evaluation provides an indication of the probability of an underlying swallowing dysfunction.

As used in this disclosure and the appended claims, the singular forms "a," "an" and "the" include plural referents unless the context clearly dictates otherwise. Thus, for example, reference to "an amino acid" includes a mixture of two or more amino acids, and the like.

As used herein, "about" is understood to refer to numbers in a range of numerals. Moreover, all numerical ranges herein should be understood to include all integer, whole or fractions, within the range. All dosage ranges contained within this application are intended to include all numbers, whole or fractions, contained within said range.

As used herein, "animal" includes, but is not limited to, mammals, which include but is not limited to, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals that are capable of the effect exhibited or intended to be exhibited by the context of the passage.

As used herein, "effective amount" is an amount that prevents a deficiency, treats a disease or medical condition in an individual or, more generally, reduces symptoms, manages progression of the diseases or provides a nutritional, physiological, or medical benefit to the individual. A treatment can be patient- or doctor-related.

As used herein, "elderly" means a human that is sixty-five years of age or older, or at least seventy-five years of age or older.

While the terms "individual" and "patient" are often used herein to refer to a human, the present disclosure is not so limited. Accordingly, the terms "individual" and "patient" refer to any animal, mammal or human having or at risk for a medical condition that can benefit from the treatment.

As used herein, "food grade micro-organisms" means micro-organisms that are used and generally regarded as safe for use in food.

As used herein, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

The term "microorganism" is meant to include the bacterium, yeast and/or fungi, a cell growth medium with the microorganism, or a cell growth medium in which microorganism was cultivated.

"Nutritional compositions," as used herein, are understood to include any number of optional additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. See, Salminen S, Ouwehand A. Benno Y. et al., *Probiotics: how should they be defined*?, Trends Food Sci. Technol. 1999:10, 107-10. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition.

Dysphaia and Aspiration

Dysphagia is the medical term for the symptom of difficulty in swallowing and refers to any deglutition (swallowing) disorder, which may include, for example, abnormalities within the oral, pharyngeal and esophageal phases of swallowing. Dysphagia is common in individuals having neurological impairment due to cerbral palsy, cerebrovascular accident, Parkinson's Disease, brain injury, stroke and multiple sclerosis. Dysphagia is also common in individuals having surgical treatment for a preexisting condition such as throat cancer, cancer of the tongue and/or mouth, or other conditions requiring oral surgery for treatment.

Esophageal dysphagia affects a large number of individuals of all ages, but is generally treatable with medications and is considered a less serious form of dysphagia. Esophageal dysphagia is often a consequence of mucosal, mediastinal, or neuromuscular diseases.

Oral pharyngeal dysphagia, on the other hand, is a very serious condition and is generally not treatable with medication. Oral pharyngeal dysphagia also affects individuals of all ages, but is more prevalent in older individuals. Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervations of the swallow reflex. It is also common for individuals with progressive neuromuscular diseases, such as Parkinson's Disease, to experience increasing difficulty in swallowing initiation.

The consequences of untreated or poorly managed oral pharyngeal dysphagia can be severe, including dehydration, malnutrition leading to dysfunctional immune response, and reduced functionality, and airway obstruction with solid foods (choking) Severe oral pharyngeal dysphagia may require nutrition to be supplied by tube feeding. Dysphagia can be dangerous because it can often lead to aspiration.

Aspiration refers to the entry of foreign material into the airway during inspiration and can manifest itself in many ways. For example, the individual may begin to perspire and the face may become flushed. Alternatively, the individual may cough subsequent to swallowing. In "silent" aspiration, there are no overt clinical or easily recognizable signs of bolus inhalation. Aspiration can cause serious health concerns including chronic lung disease, aspiration pneumonia, dehydration and malnutrition. As such, dysphagia and aspiration can dimish the quality of life for people of all ages, comprising not only medical, but social, emotional and physical well-being.

Anatomical Structures Associated with Dysphaia

There are several anatomical structures that are most likely to be associated with impaired swallowing safety and are indicators of a patient's risk of aspiration. Some of these anatomical structures include, for example, respiration, the jaw, lips, soft palate, tongue, hyoid, epiglottis, larynx, pharynx and upper esophageal sphincter ("UES"). To determine sufficiency of swallowing parameters, a number of parameters can be investigated including, but not limited to, lip closure, jaw closure, anchoring of the tongue, tongue lift, tongue control, tongue sweep, tongue seal, soft palate seal, mouth breathing, nasal breathing, lingual propulsion, tongue pressure, laryngeal elevation, hyoid movement, hyolaryngeal excursion, upper esophageal sphincter opening, epiglottis movement, larynx opening, vocal fold closure, laryngeal sensation, pharyngeal contraction, pharyngeal fatigue, laryngeal adductor reflex, laryngeal fatigue, respiration halting, respiration recommencement, and pharyngeal sensation. A safe and efficient swallowing system requires a bolus to pass swiftly and efficiently through the oral cavity and pharynx into the esophagus while bypassing the airway.

Respiration

The respiratory system is, strictly speaking, not part of the swallowing system. However, the inter-relationship between the respiratory and swallowing systems is critical for determining an individual's risk for aspiration. There is a preferential coupling of swallowing with the expiratory phase of respiration, both before and after the swallow. Due to the biomechanics of the strap muscles connecting the jaw and tongue base to the hyoid and the hyoid, in turn, to the larynx, these muscles are best placed to work efficiently during swallowing when the body is in an exhalation phase. In addition to the biomechanical "assistance" offered to the strap muscles, the exhalation post swallow also allows for any potential residue in the pharynx to be swept upwards towards the mouth and pharynx, and away from the airway. Any abnormality of resting respiration such as respiratory rate or rapid, high velocity or chaotic patterns will increase the chance of aspiration.

Inhalation after the swallow is rarely seen in healthy individuals, except in circumstances that involve swallowing large volumes (e.g., 100 ml). Inhalation is, however, seen in individuals with dysphagia. Swallows that are not bounded on either side by exhalation are, in general, more likely to display abnormality. Inconsistency in swallow-respiratory pattern between swallows within the same individual, is also considered deviant.

Lung volume plays a little known, yet important role in swallowing efficiency. In this regard pharyngeal transit time is impaired if lung volume is low. Lung volume will be affected by the phase of respiration (inhalation or exhalation) in which swallowing occurs.

Breathing stops ("apnea") during the act of swallowing as the bolus passes through the pharynx. Apnea duration increases as we age, is a common condition among the elderly, and is not a consequence of closing the vocal folds. Individuals who have had their larynx removed and their airway separated from the pharynx, rendering aspiration impossible, continue to exhibit apnea during swallowing. Apnea occurs before vocal fold closure and is quite independent of vocal fold closure or epiglottic deflection. Most individuals are able to swallow a 20 ml liquid bolus in one motion and maintain apnea throughout that swallow. Segmenting a bolus of 20 ml into multiple swallows may point to abnormality of function.

It is a combination of lung function, lung volumes, abnormality of swallow respiratory phase coupling, duration that the bolus dwells in the pharynx at any point during the swallowing process, and variability of apnea duration that best predicts aspiration from this domain.

Measures of respiratory function fall into two categories: (a) measures of chest wall function (strain gauges around the rib cage and abdomen); and (b) nasal airflow measures. Chest wall measures may be difficult with people who are very unwell or those with muscular weakness preventing upright positioning (such as post stroke). Two different types of nasal cannula have been reported. One variety uses micromanometers to measures changes in direction of airflow, whilst the other (thermistor) detects changes in temperature during inhalation and exhalation. Exhaled air is warmer than inhaled air. The thermistor emerges as the better of the two devices. Patients who are habitual mouth breathers or those with nasal defects will provide unusual data. Patients requiring supplemental oxygen via nasal prongs will also prove a challenge for using this type of technology. Some investigators have recommended concurrent use of measures of nasal airflow and respiratory effort (chest wall). Acoustic analysis of respiratory sounds and swallowing sounds has also been reported. Using signal processing that can differentiate the two types of signals may prove beneficial as a screening method for determining respiratory phase (e.g., end expiration, inspiratory/expiratory, end inspiration, etc.).

Lip and Jaw

The jaw (or mandible) facilitates approximation of the teeth and lips during mastication and swallowing. The lips play a role in removing food from a utensil and channeling liquid into the oral cavity. The lips are active participants during swallowing, not passively closed during oral containment and propulsion. There is wide inter-individual variation in lip movement amplitude and duration. Conditions where the lips remain open, (e.g., muscular weakness of the jaw as seen in cerebral palsy), co-occur with increases in the occurrence of a high arched palate, tongue thrust and mouth breathing.

When the lips remain open, the muscles of the jaw must be assessed because jaw closure facilitates lip closure. Prosthetic devices that artificially lower the palate and improve tongue-to-palate contact have also been shown to improve lip closure, as well as swallowing efficiency and safety. The presence and "fit" of dentures can increase oral transit time, with the muscles of the lips and lower face being recruited to stabilize the dentures. As the muscles engage in stabilization activities, their role in food processing and swallowing is made more complicated and hence the oral stage is slowed. Increased oral transit time should be anticipated with elders who have dentures, and particularly those with poorly fitting dentures.

Closure of the jaw brings the tongue within physical proximity of the palate, a necessary biological position for swallowing. The jaw acts like a platform from which the tongue is able to move independently. During the swallow, jaw movement is minimal, acting as a stabilizer for the tongue. Poor stability of the jaw will have an effect on tongue efficiency and accuracy. During mastication and liquid swallowing tongue and jaw movements are linked but not necessarily in exact phase.

During chewing the presence of teeth provides biomechanical stability for the jaw. Sensory information from the teeth and periodontal receptors either promote or inhibit chewing. For chewing of solids, it appears that it is the volume of particles rather than particle size that determines chewing response.

The jaw has complex connections to the rest of the swallowing mechanism. An open-mouth posture (e.g., 5-6 mm) increases respiratory rate. The strap muscles above and below the hyoid bone (supra and infrahyoids), are affected by jaw movement.

The lip muscles have been investigated using surface electromyography or devices akin to a builder's level to measure degree of placement away from midline. Jaw function has been assessed by electromyography of muscles used to move the jaw, multiple camera views of jaw markers, and videofluoroscopy. Of course, simple observation of open-mouth posture and soft facial features suggestive of weakened muscles should not be discounted.

Soft Palate

The soft palate has a three-fold role in swallowing: (a) it provides a physical barrier between the nasal and oral cavities; (b) it forms a pressurized seal that facilitates a downward pressure gradient during bolus propulsion by the tongue; and (c) provides a nasal route for an airway during chewing and during lip and jaw closure during swallowing. Patient preference for mouth breathing over nasal breathing may indicate some level of respiratory disorder involving the nasal passage. It may also indicate a physiological need to decrease "work of breathing." Open-mouth posture helps to decrease the work of breathing. For example, with the increased cardiac load that occurs for healthy people during running, it is easier to breathe through the mouth, lips slightly apart, than nasal breathing with lips closed. Similarly with cardiac conditions, patients may revert to mouth breathing to reduce their work of breathing.

The soft palate houses both fast and slow twitch muscle fibers. Swallowing preferentially activates fast twitch, fast fatigue fibers whereas speech preferentially activates slow twitch fatigue resistant fibers. Methods of assessing soft palate function for speech are inappropriate for predicting soft palate function during swallowing.

The palatoglossus muscle is critical for generating a closed pressure system required for effective sucking. The palatoglossus muscle has its origin on the undersurface of the soft palate and its insertion on the sides of the tongue. It is responsible for constriction of the passage between the soft palate and the base of tongue (fauces or glossopalatal junction). The muscular links between the soft palate and the tongue confirm the central importance of tongue function for swallowing safety and efficiency. The principle role of the soft palate in swallowing is to close off the nasal pathway and in so doing, to assist in the creation of a pressurized region that will preferentially direct the bolus downwards toward the pharynx. Failure of soft plate elevation and closure allows nasal regurgitation, and decreases the efficiency of the swallow. It places more demand on the tongue to propel the bolus and on the pharyngeal constrictors to clear the tail without leaving residue.

Soft palate function can be viewed using, for example, videofluoroscopy, and has been more invasively investigated using hooked wire electrodes. Function during speech, such as during production of the sound "ahhh" does not provide a valid indication of function during swallowing due to different activation of fast twitch, fast fatigue (sprint) fibers for swallowing and slow twitch, slow fatigue (long distance) fibers for speech.

Tongue

The tongue plays a crucial role in both the oral and pharyngeal phases of swallowing. For liquids, during the oral phase, the tongue tip (or blade) is described to sit either behind the mandibular teeth in a "dipper" position, or more commonly behind the maxillary teeth, contacting the alveolar ridge, in the so-called "tipper" position. Both of these positions occur in healthy individuals, although it has recently been recognized that the use of a "command to swallow" is more likely to trigger a tipper posture. The back of the tongue is also raised towards the palate, creating a sphincter-like high-pressure zone. A pocket-like chamber is created in the midline along the groove of the tongue, to house the liquid bolus. In order to transfer the liquid bolus back towards the pharynx, the tongue body and dorsum (back of tongue) move forwards along the palate, bunching towards the tongue blade. This action works like a conveyor belt to squeeze the liquid bolus posteriorly between the dorsal surface of the tongue and the palate.

The tongue aids in positioning the bolus on the occlusal surface of the molar teeth, and in collecting particles of processed food and bringing them back to midline. During chewing, the tongue and the jaw cycle in an anti-phase relationship, which avoids trauma to the tongue. This mechanical action of a-piston-like structure (the tongue) protruding and retruding in a cyclic pattern between the opening and closing jaw serves to "pull-back" chewed particles into the upper pharynx, where they collect in the vallecular space. Liquids also appear to collect in the vallecular space if they are chewed, rather than being squeezed back by the tongue, and also appear to collect in the pharynx for infants during breast or bottle-feeding, and in adults during sequential continuous swallowing, for each swallow after the initial swallow in the series, and during straw drinking.

It has been argued that because laryngeal elevation is maintained throughout a series of sequential swallows, there is a reduced risk of aspiration and, therefore, no biological need to avoid liquid collection in the pharynx. Similarly, in straw drinking, the maintenance of apnea throughout several swallows may mean that there is less risk of aspiration if a liquid bolus collects in the pharynx. It is important to note whether single or continuous swallows are being investigated, as the physiology of each is slightly different. Failing to differentiate the discrete from continuous boluses may cause labeling of a normal event as something pathological.

With both liquid and solid stimuli, the pharyngeal phase of the swallow involves a backward-downward sweep of the tongue. With liquids, the compressed oral tongue extends again to its full length. The body and dorsum of the tongue travel backwards and achieve cavity constriction against the posterior palate and then against the constricting pharyngeal walls behind the tail of the bolus. There is some evidence that occlusion with the pharyngeal lumen is a phenomenon that can involve variable and differential contributions of the tongue base and the pharyngeal musculature, analogous to lip closure involving variable contributions of the upper and lower lip, depending on the circumstances. In particular, it has been shown that when the front of the tongue is anchored in a forward position between the teeth, this restricts the degree of posterior movement that can be achieved by the tongue base, and results in compensation by the posterior pharyngeal musculature in order to achieve tongue-to-pharyngeal wall constriction.

With respect to penetration-aspiration risk, there are two primary aspects of tongue function that need to be considered. The first is the ability of the tongue to contain the liquid bolus in the mouth, preventing it from spilling into the pharynx in an uncontrolled manner. The second is the degree to which bolus driving forces that are created through tongue-palate and tongue-pharyngeal-wall contact and pressure generation are adequate to propel the bolus through the pharynx in entirety, without leaving post-swallow residue behind. For these reasons, a particular interest in measuring tongue-palate pressure generation capacity has emerged in the literature.

Measurement of tongue function can be made using somewhat invasive measures. Transducers may be embedded in an acrylic palate with measures occurring as the tongue sweeps along the transducers, or pellets are glued to the tongue using a biomedical adhesive and tracked using x-ray microbeam or electromagnetic methods.

Hyoid

The hyoid bone is an anchor point held in position above by connection to the floor of mouth and tongue, below by the larynx and major strap muscles of the neck and posteriorly by the middle pharyngeal constrictor. The hyoid moves in an upward (superior) then forward (anterior) direction during swallowing. Anterior movement is particularly critical. It is linked to posterior tongue-palate pressures, geniohyoid muscle contraction, epiglottic deflection, UES opening and swallowing safety. The connection between the jaw, tongue and hyoid require the synchronous movement of this set to bring up and stabilize the "platform" of the jaw and hyoid to allow the "gymnast" of the tongue to perform its role. The pulley-like connections from hyoid to larynx go on to facilitate opening of the UES. Without hyolaryngeal excursion, UES opening is minimal and residues in the pyriform sinus are often seen. When anterior hyoid movement is significantly reduced there is an increased risk of penetration-aspiration.

Surface electromyography ("sEMG") is a non-invasive way of measuring muscle activity associated with hyoid movement in swallowing. This signal provides a composite picture of muscle activity that is temporally accurate. Amplitude measures cannot be meaningfully extracted from these signals.

Dual-axis swallowing accelerometry holds promise as a non-invasive technology for capturing accurate measures of hyoid movement in both temporal and magnitude domains. However, these measures must be made after appropriate filtering to remove motion artifact. Signal processing classifiers hold promise for discriminating aspiration using dual-axis accelerometry.

Epiglottis

The epiglottis is a leaf-like cartilaginous structure that separates the tongue base from the laryngeal vestibule. During swallowing, it falls from an upright position to a horizontal position, and the tip of the epiglottic leaf folds over the entrance to the airway. However, it does not form an airtight seal. The epiglottis acts more like a rock in a stream, designed to direct flow around it. The liquid bolus flow is more likely to be turbulent due to its propulsion under pressure. In the pharynx, epiglottic deflection directs the bolus to flow around the larynx, and into the pyriform sinuses. Once past the larynx, it can then continue its passage through the UES. These epiglottic movements are most likely the passive results of other structural movements in swallowing, most notably movements of the tongue-base, hyoid and larynx. There is no noninvasive way to measure epiglottic movement during swallowing.

Larynx

The larynx opens above into the pharynx. It is attached to the lungs below via the trachea. The vocal folds, housed within the larynx, have been thought of as a valve-like barrier during swallowing to prevent material from entering the airway (aspiration). However, the vocal folds do not always form an entire seal along their length. In fact, hyolaryngeal excursion is more important to swallowing safety than vocal fold closure. On this point, poor anterior hyolaryngeal movement is more likely to result in penetration/aspiration and pharyngeal residue.

Perhaps due to the technologies commonly used to assess swallowing such as videofluoroscopy, assessment largely focuses on movement. In regards to the larynx, sensation is equally important. Impairment of both laryngeal sensation and pharyngeal contraction significantly increases risk for aspiration and penetration for both liquids and purees. Preserved laryngeal sensation plus poor pharyngeal contraction results in smaller incidences of both penetration and aspiration. Thus, it appears that laryngeal sensation is a critical factor for penetration/aspiration risk.

Penetration is not uncommon in healthy individuals, and is more likely to be seen in individuals over the age of 50 years and, particularly, the elderly. In healthy individuals, the penetrated bolus is often ejected spontaneously. Frequency and depth of penetration (closeness to the vocal folds) becomes important over the course of a meal where fatigue is a factor. Aspiration on a single swallow does not predict frequency of aspiration. For some individuals, only one aspiration in a series of six swallows was noted.

The hierarchy of laryngeal risk factors for aspiration includes: (a) impaired pharyngeal contraction plus impaired laryngeal sensation; (b) impaired laryngeal sensation (absent or diminished laryngeal adductor reflex); (c) reduced closure of the false vocal folds; (d) reduced closure of the true vocal folds; and (e) age (e.g., over 50 years).

Regarding assessment, although videofluoroscopy provides the best-known method of documenting penetration, aspiration, and laryngeal movement, sensory testing of the laryngeal region emerges as a necessary co-assessment based on the literature. As noted above, reduced laryngeal sensation is a prime risk factor for laryngeal aspiration. At present, technology such as fiberoptic endoscopic evaluation of swallowing with sensory testing ("FEESST") is used for this purpose. However, even with experience in conducting the procedure, there is only moderate inter-rater reliability, throwing caution to interpretation of results.

Pharynx and Upper Esophageal Sphincter

The pharynx is a funnel-shaped tubular cavity, bordered anteriorly by the tongue-base, the epiglottis and the posterior (arytenoid) surface of the larynx/trachea. The posterior and lateral walls of the pharynx are made up of a basket-weave type arrangement of vertically, horizontally and obliquely oriented muscles. The pharyngeal constrictor muscles (superior, middle and inferior) wrap horizontally around the circular lumen of the pharynx.

Anatomically, it is important to note that the pharynx contains pockets that can collect bolus residues. The vallecular space is a pocket along the anterior wall of the pharynx, between the tongue base and the epiglottis. The pyrifonn sinuses are pockets at the bottom the pharynx, which sit on either side, above the UES. The UES (or pharyngo-esophageal segment) itself is a ring of muscle, incorporating the cricopharyngeus muscle, which is typically contracted and closed at rest. In a healthy swallow, EMG studies show that the activity of the cricopharyngeus muscle is inhibited just prior to opening of the UES. This is primarily attributed to the biomechanical effects of suprahyoid and infrahyoid muscle contraction on the front wall of the sphincter. The opening of the UES creates a negative pressure zone, which may create a suction-like effect to facilitate bolus movement into the esophagus, although the literature is somewhat divided on the question of whether a hypopharyngeal suction pump exists.

Bolus transport through the pharynx occurs primarily as the result of tongue propulsion (driving forces), and the shortening of the pharynx, which occurs via contraction of the suprahyoids, infrahyoids and vertically oriented pharyngeal muscles. Contraction of the pharyngeal constrictor muscles creates a peristalsis-like wave of lumen closure that chases the tail of the bolus downwards through the pharynx. Of these two actions (shortening and constriction), shortening is more important to efficient bolus transport and swallowing safety.

There do not appear to currently be any non-invasive measures of pharyngeal bolus transport and clearance that are valid and reliable. Measures of hyoid and laryngeal movement will provide reasonable proxy information regarding the shortening of the pharynx while measures of posterior tongue pressure may provide reasonable information regarding the bolus driving forces that appear to be primary factors for pharyngeal bolus clearance.

Detection of Dysphagia

It is estimated that approximately 80% of patients with dysphagia remain undiagnosed. A primary reason for the large number of missed diagnosis is that general practitioner's offices and nursing homes are relatively ill-equipped to diagnose these types of conditions. In many instances, the tests available at these locations are either expensive, time-consuming, invasive, only available in specialist centers and/or expose the patient to ionizing radiation. For example, the current gold standard diagnosis for dysphagia and aspiration is videofluoroscopy, where a patient ingests barium-coated material and a video sequence of radiographic images is obtained using x-rays. This test is not only invasive and costly in terms of time and labor, but also exposes the patient to potentially harmful ionizing radiation.

Fiberoptic endoscopy, pulse oximetry, cervical auscultation and swallowing accelerometry are just a few examples of additional tests used to detect dysphagia/aspiration. Fiberoptic endoscopy is another invasive technique in which a flexible endoscope is inserted transnasally into the hypopharynx. It is generally comparable to the modified barium swallow in terms of sensitivity and specificity for aspiration identification. Pulse oximetry is a non-invasive adjunct to bedside assessment of aspiration, and cervical auscultation involves listening to the breath sounds near the larynx by way of a laryngeal microphone, stethoscope or accelerometer placed on the neck. Cervical auscultation is generally recognized as a limited, but valuable, tool for aspiration detection and dysphagia assessment in long-term care.

Swallowing accelerometry is similar to cervical auscultation, but has entailed digital signal processing and artificial intelligence as discrimination tools, rather than trained clinicians. Accelerometry has demonstrated moderate agreement with videofluoroscopy in identifying aspiration risk, whereas the signal magnitude has been linked to the extent of laryngeal elevation. However, prior art swallowing accelerometry only provides limited information in classifying normal from "dysphagic" swallows and does not provide broader information about the clinical status of the patient.

Technologies that target tongue, and respiratory function in particular are required for detection of dysphagia and/or related aspiration. Lung function can be assessed as part of routine medical appointments using validated technologies already found in the doctor's office (e.g., spirometer). Individuals who present with abnormal spirometric findings for total lung capacity and inspiratory capacity should be questioned regarding their ability to swallow foods, liquids and medications (e.g., using the EAT-10). Measures of resting respiratory rate can be made by observation, counting the number of respirations over a one minute interval. This is a standard medical observation, but one that doctors have not previously linked with swallow-respirator coordination.

Dual-axis acclerometry has been identified as a screening tool for further development to determine normal from abnormal swallows. This technology has been used for the assessment of children, young, middle aged and healthy individuals. Both healthy and dysphagic individuals have been assessed. The technique has been validated against videofluoroscopy and endoscopy. This technique appears to be useful, both for the quantification of hyolaryngeal movement in swallowing, and for aspiration detection through the use of signal processing classifiers.

Technologies that provide information about tongue function are also required. The tongue is identified as a critical element for swallowing efficiency. Devices that allow strain gauges to be placed in an acrylic palate (like a mouth guard) provide valid information about tongue-palate contact and pressure timing on the palate. This type of device does not lend itself to use in a doctor's surgery though due to individuality of palatal shape and time and costs associated making the acrylic palate and sterilization requirements. Air-filled pressure bulbs provide an alternative, with the registration of intra-oral pressure amplitude and timing, similar to pressures experienced by the bolus, even in the absence of full tongue-palate contact. However, the use of bolus-sized air-filled bulb systems for measuring pressures should probably be restricted to the context of saliva swallows, since the combination of a bulb and a bolus may exacerbate safety risks in individuals with dysphagia.

Surface electromyography ("sEMG") of the muscles under the chin and along the neck can provide information regarding muscle contraction timing, and, by proxy, structural movement. However, this technology is not sensitive enough to provide information regarding the contraction of specific muscles responsible for anterior hyolaryngeal movement, which has been identified as a key risk factor for aspiration. In addition, sEMG amplitudes cannot be interpreted easily due to a variety of signal placement and signal-damping factors that exist across individuals. The time associated with applying the electrodes and training to use and interpret this technology is likely to be a large barrier to most doctors in general practice or geriatric specialty. Although reduced laryngeal sensation has been identified as a risk factor for aspiration, the ability to measure this non-invasively does not currently exist.

In view of the short-comings of the prior art devices for diagnosing dysphagia, it would be advantageous to develop improved methods of diagnosing and detecting dysphagia that are flexible, lightweight, non-invasive, cost effective, and capable of cooperating with electronic technologies.

Improved Dysphagia Diagnostics

Applicants have developed novel apparatuses and methods for detecting parameters associated with swallowing dysfunction and diagnosing dysphagia and/or aspiration. In a general embodiment, the present disclosure provides for sensors and databases that cooperate to diagnose a swallowing dysfunction. The database may be a database having a statistically-significant amount of data derived from swallowing profiles of a large number of healthy and dysphagic patients. The sensors may be known sensing devices such as videofluoroscopy ("VF"), electromyography ("EMG"), etc., or may be the improved sensors disclosed herein.

In an embodiment, and as illustrated in FIG. 1, the present disclosure provides a smart sensor device 10 that may be used for multi-parametric dysphagia analysis. Device 10 includes, for example, a flexible substrate 12 to which various electronic elements are added. In this regard, substrate 12 may include a microcontroller 14 with communication capabilities, an antenna 16, and printed sensors 18. Devices 10 may be placed directed on the skin of an individual for purposes of sensing non-invasive parameters associated with a patient's swallowing profile (e.g., acoustic, motion, EMG, etc.), which may be indicative of an underlying swallowing disorder. The flexible substrate 12 and the microcontroller 14, the antenna 16 and the printed sensors 18 positioned thereon are preferably encased in a plastic foil 13.

In an embodiment, devices 10 are wearable by an individual and are placed directly on the neck, throat, or surrounding areas, to detect, for example, epidermal vibrations, swallowing sounds, pressure changes, etc. that occur during swallowing. As such, devices 10 may include a layer of adhesive (not shown) to adhere devices 10 to the patient. The adhesive should be approved by the Food and Drug Administration ("FDA") and should be removable from the skin, while also having enough adhesive power to remain in place during diagnostic testing. The skilled artisan will also appreciate that devices 10 need not be adhered using adhesive, but may instead by secured using other means such as rubber bands, straps, etc.

Figure 3:
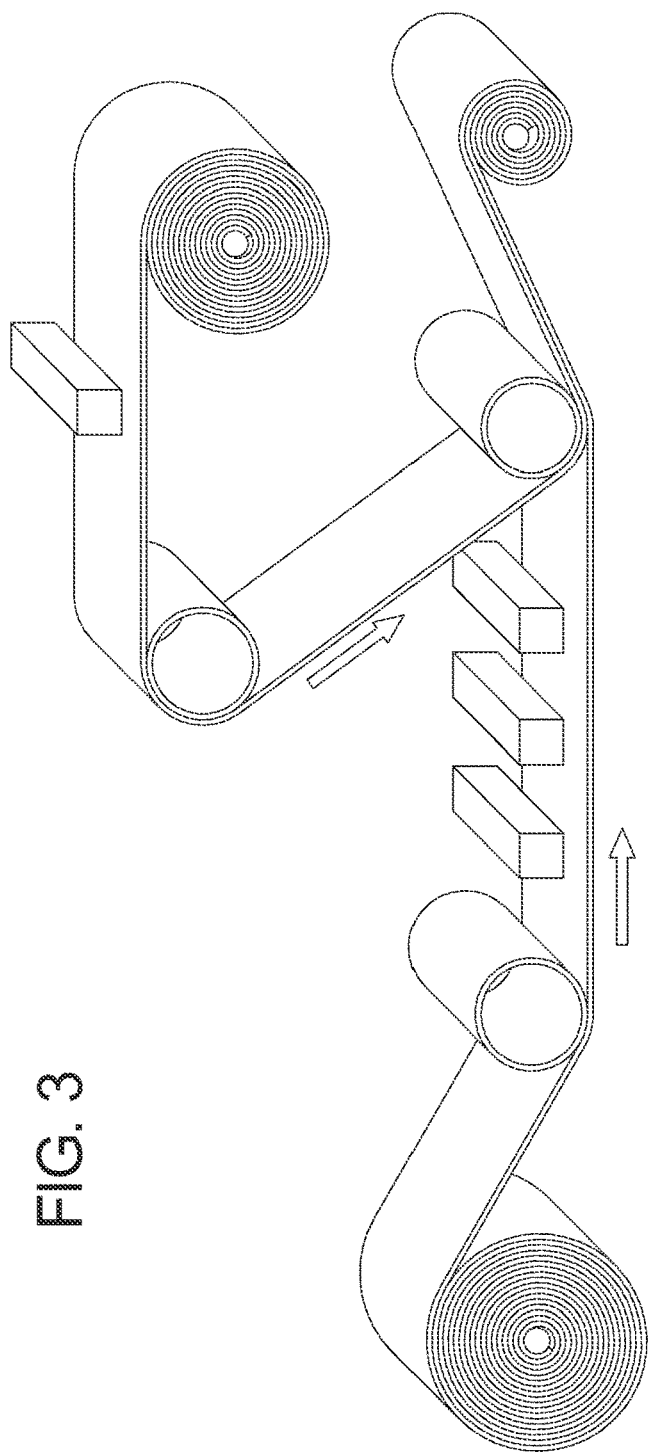
FIG. 3 illustrates a schematic of a process for manufacturing a sensor device in accordance with an embodiment of the present disclosure.

Devices 10 have a number of advantageous physical properties. For example, devices 10 are flexible and comfortable so as to shape to a patient's neck, throat or surrounding areas, and are thin, planar, and flat for discretion when in use. It is importance for devices 10 to also be lightweight to avoid interference with measurements when in use. Because of these advantageous physical properties, it is possible to manufacture devices 10 that are low-cost, but are produced in high volumes. Devices 10 may be manufactured using roll-to-roll manufacturing processes, as schematically represented in FIG. 3, and as will be discussed further below.

The materials used to manufacture devices 10 of the present disclosure may be relatively low-cost. For example, devices 10 may be manufactured using polymers and printed electronics. The polymers typically include, for example, polyethylene napthalate ("PEN"), polyethylene terephthalate ("PET"), and/or like polymers, and provide devices 10 with flexibility and reduced manufacturing costs.

Devices 10 may also be manufactured using printed electronic technologies. As mentioned above, the electronic components of devices 10 include, for example, a microcontroller 14, an antenna 16 and at least one printed sensor 18. Printed sensors 18 can sense any number of non-invasive parameters that are associated with a patient's swallowing profile, and may be indicative of a probability that the patient has an underlying swallowing dysfunction. For example, printed sensors 18 may sense pressure, sound waves, acceleration, velocity, distance, electrical current or voltage, electromagnetic radiation, temperature, etc. In an embodiment, printed sensor 18 is an accelerometer. In another embodiment, printed sensor 18 is a microphone. In another embodiment, printed sensor 18 is a thermometer. As used herein, "acoustic" includes at least vibration, sound, ultrasound, and infrasound.

Devices 10 may be either reusable or disposable. In an embodiment wherein devices 10 are reusable, devices 10 must be able to withstand sterilization conditions when devices 10 are cleaned and sterilized between uses with different patients. In an embodiment wherein devices 10 are disposable, it is important that the cost of devices 10 is low enough that it is feasible and economical to dispose of devices 10 after just one use, or after a limited number of uses with the same patient. In an embodiment, devices 10 are disposable. In another embodiment, devices 10 may be sold at a cost of about fifty cents to about two dollars. In an embodiment, devices 10 may be sold for one dollar.

Antenna 16 of devices 10 may act as a transmitter and/or receiver to send or receive electronic signals. For example, in an embodiment, antenna 16 acts as a transmitter. In such an embodiment, device 10 may be placed on the neck/throat of a patient, and used to detect at least one parameter associated with the patient's swallowing profile. Once the swallowing parameter has been measured, antenna 16 may act as a transmitter to wirelessly send the measured parameter data to a processing device 20 to log and evaluate the data. Alternatively, antenna 16 may act as a receiver to receive electronic signals from a transmitter or processing unit 20.

Figure 2:
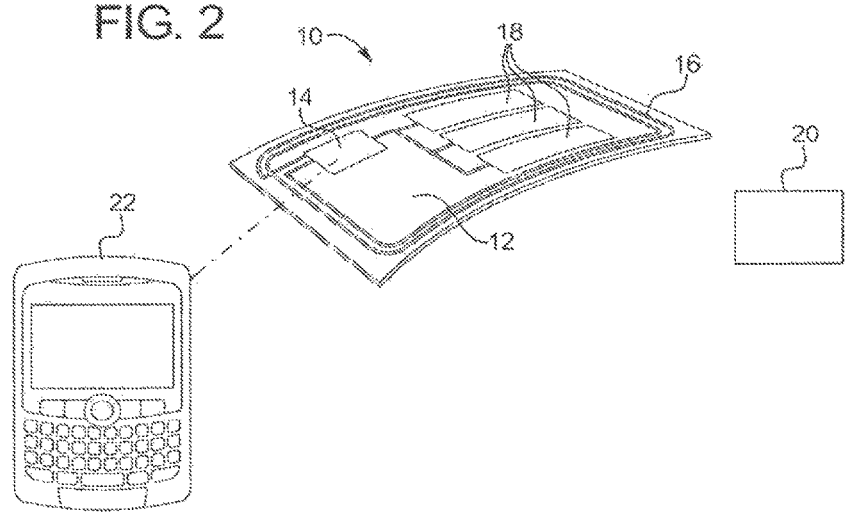
FIG. 2 illustrates a sensor device in accordance with an embodiment of the present disclosure.

The skilled artisan will appreciate, however, that including transmission/reception functions on devices 10 may be somewhat costly and may prohibit the disposable nature of devices 10. Therefore, to reduce costs associate with devices 10, and in another embodiment as shown in FIG. 2, devices 10 may be wired to a second device 22 that is capable of transmitting an electronic signal to a processing device 20. Second device 22 may be any electronic device capable of sending and/or receiving electronic information such as, but not limited to, an iPod, an iPhone, an iPad, a cell phone, a personal digital assistant ("PDA"), a pager, a short message service ("SMS") system, a Blackberry, etc. In this embodiment, devices 10 obtain the measured parameters, and wire the measured parameter to second device 22, which transmits the measured parameter to processing unit 20.

As such, the skilled artisan will appreciate that devices 10 may communicate data via wired connections or wirelessly. Any wireless communication disclosed herein will be understood to include any wireless communication pathway (e.g., form of energy) including, for example, radio frequency, infrared light, laser light, visible light, acoustic energy, radio waves, etc. In an embodiment, the wireless communication is Bluetooth technology. In another embodiment, the wireless communication is a cellular telephone network.

The skilled artisan will understand that processing devices 20 of the present disclosure are constructed and arranged to cooperate with software that is configured to execute many of the processes discussed herein. For example, the software may be configured for data acquisition and gathering, database updating, evaluating and comparing data points, storing data and wired and wireless transmissions of data, among others.

As mentioned briefly above, the sensors of the present disclosure need not be devices 10 and may be any other sensor known in the art and useful for sensing parameters associated with a patient's swallowing profile. In the case where known sensor devices are used, a swallowing signal (e.g., swallowing sounds, pressures, velocities, etc.) is generated by the known sensor device and then output to either the compiled database described above, or an interpretive algorithm capable of evaluating the sensor output. The known devices that may be used for measuring a swallowing signal may include, but are not limited to, videofluourscopy, acoustic, acceleration, velocity, distance, electromyography, mechanical myography, electrical, thermographic/temperature, or combinations thereof. In this embodiment, the signal generating device (EMG) actually takes and processes the measurement. This is distinguishable from the use of devices 10 of the present disclosure, wherein devices 10 measure the signal and transmit the signal to a signal processing unit that may be remote from device 10 such as, for example, an algorithm residing on a remote server. Going forward, a "sensor" discussed herein may be either the sensors 18 of device 10 or sensors built into known devices such as EMG, unless otherwise specified.

In use, a sensor is placed on the skin of a patient, and is used to obtain swallowing data from the patient's swallowing profile. This data may include, as discussed above, acoustics, velocity and temperature of the patient's unique swallowing mechanics. Epidermal vibrations, swallowing sounds and pressure changes are just a few examples of data detected by the sensors that make-up the acoustic profile of the patient's swallow. The sensors may be used in a variety of ways to obtain measurements related to a patient's unique swallowing characteristics, and to characterize and predict swallowing dysfunctions.

For example, in a first embodiment, sensors may be used in combinations with a device to output electronic signals corresponding to a characteristic of a patient's swallowing profile to a pre-existing database for comparison with known swallowing dysfunction data and to diagnose a potential swallowing impairment. In this regard, a patient's swallowing profile may be calibrated and compared against a comprehensive database, which can indicate any dysfunction in the patient's swallow. Thus, the sensor and database combination is able to provide a precise diagnosis of the nature of the patient's swallowing difficulty and a recommended therapy. As a result, the complete system, including the sensors and database, can be used in swallowing rehabilitation as a biofeedback.

In another embodiment, sensors in combination with devices may be used to output signals corresponding to at least one swallowing parameter of a patient's swallowing profile that is fed to an interpretive algorithm, which is able to evaluate the data for swallowing dysfunctions. Thus, in the absence of a database, the measurements obtained using sensors can be used to construct an interpretative algorithm that models the probability of an underlying swallowing dysfunction and risk of dysphagia.

Both the database and algorithm are used to log and evaluate the swallowing profiles of many healthy patients and many dysphagic patients. By modeling the swallowing profiles of healthy patients, "normal" ranges for different parameters associated with swallowing are able to be determined. By modeling the swallowing profiles of dysphagic patients, it is then possible to determine how far outside of the normal ranges dysphagic patients are and, alternatively, what constitutes "normal" ranges for different parameters associated with a dysphagic patient's swallowing profile.

The pre-existing database may be located in any location, and may include information obtained over many years that relates to dysphagia and aspiration. The database may be any type of database and may be located in proximity to or remote from the patient. For example, the database may be a database of a computer or processing device located in or near to a patient testing device. Similarly, the database may be located in the same building as the patient and patient testing device. Alternatively, the database may be a central database that is located remote from a patient testing device. Such a central database is capable of gathering data from a remote user site having measured parameters and data specific to any number of patients. The skilled artisan will appreciate that any database capable of cooperating with the hardware and software of a processing device may be used. Depending on where the patient testing is performed, the adjacent and/or remote locations may be, for example, a care giver's office, a physician's office, a clinic, a hospital, a nursing facility, a specialty clinic, or a long-term care facility. In an embodiment, the remote location is mobile. Such a mobile location refers to, for example, a home health care provider, a clinic on wheels, a flying care clinic, etc. Regardless of its location, the database may be used by one patient testing site, or may be used by more than one patient testing site.

As mentioned above, the database may include information obtained over many years that relates to both healthy patients and patients having swallowing dysfunctions such as dysphagia and aspiration. The database may be comprised of data obtained from measurements made with, for example, videofluouroscopy ("VF") tests run over a number of years, and may include data from a number of healthy and dysphagic patients.

In an embodiment, the data contained in the database has been accrued over a time period of at least 5 years, or at least 10 years, or at least 20 years. In another embodiment, the data contained in the database has been obtained from a patient population of at least 500 patients, or at least 1000 patients, or at least 3000 patients, or at least 5000 patients. Regardless of the number of tests run or patients tested, the database should include a statistically-significant data set that is of sufficient size, is science-based, and contains differential/relative measurements of absolutes. Since the database is already established, and devices 10 can be relatively inexpensive to manufacture, it is relatively inexpensive to provide such a system to, for example, a general practitioner for use in his or her office.

As discussed above, the swallowing profiles of healthy patients are logged and evaluated to serve as a baseline comparison for the swallowing profiles of potentially dysphagic patients. Various parameters associated with the swallowing profiles may be included in the database. For each parameter (e.g., time-of-flight) there may be, for example, at least 5000 measurements. Plotting each of the measurements on the same curve provides a Gaussian distribution of a small number of possible dysfunctions. That is, 5000 measures of dysphagic patients, representing 25 underlying diseases, may be "translated" to three or four discrete Gaussian curves. There may also be, for example, two methods of recording baseline healthy data: a) truly healthy during initial videofluouroscope measurement; and b) "composite" healthy, wherein it is posited that, for example, for a head/neck cancer patient, the dysfunction is apparent in the neck, leaving, for example, the lip seal functioning as per a normal individual. Using a two-part method may greatly increases the robustness of healthy data contained in the database.

Further, the database may be a continuously changing database wherein new data points (e.g., swallowing profile measurements) are entered into the database after collection. In this manner, the database will continue to grow in number and variety of data points and, as a result, will continue to improve in its accuracy of swallowing dysfunction predictions/diagnosis. As such, enhancement of the database continuously improves the evaluation methods of the present disclosure, wherein the database uses gathered information to further "learn" about potential dysfunctions and disorders. Simply by continuously providing additional data points, the database can "learn" more about normal variants for swallowing dysfunctions and disorders.

Similarly, the more information that is contained in the database, the "smarter" the database becomes. In this regard, if the database includes information relating to a pre-existing condition of the patient, the database and/or algorithm may be able to better determine whether the patient's swallowing characteristics are normal. For example, if a patient has previously undergone oral surgery to remove a cancerous portion of the patient's tongue, the patient will have "normal" swallowing characteristics that may be drastically different than a patient who has not had a portion of his or her tongue removed. Upon evaluating the sensor output and comparing the sensor output to data, the evaluation may find that the patient's swallowing characteristics, although representative of a swallowing dysfunction, are still "normal" for a patient having had such a surgery.

Once parameters associated with the patient's swallowing profile are measured, the electronic data is transferred via a wired connection or wirelessly to a processing device. For example, device 10 may send a measured parameter to processing device 20 via an electronic signal from a second device 22. Sensors may transmit the signal via a wired, or wireless connection to a device that is capable of processing the signal (e.g., a computer, any processing device, etc.). The signal processing unit can then compare the measurement to the existing data in the database, or use an interpretative algorithm to evaluate the data. Embodiments including the interpretive algorithm may be based on double-acceleration measures at 90°.

A processing unit can evaluate the sensor output in a number of ways based on the capabilities and configuration of the processing unit's software. The evaluation may, for example, translate the signal output to a meaningful value or data form, or determine if dysphagia exists, or associate the signal output with a numerical value associated with a predetermined swallowing dysfunction. In an embodiment, the evaluating compares the sensor output (e.g., measured parameter) to known disorder and dysfunction data already existing in the database. Software associated with the database may categorize the sensor output in any number of categories already established in the database with respect to known dysfunctions and disorders. Software associated with the database may also cause an interpretative algorithm to interpret the sensor output and characterize any potential dysfunction or disorder of the patient. The evaluation by the processing device may take up to 10 minutes or may be substantially instantaneous.

Since the database contains a large amount of statistically-significant information, comparison of measured parameters with known data indicative of dysfunctions and disorders is a cost-effective and time-efficient process. The evaluation occurs in a validated, sensitive, specific and reliable manner. The evaluation may occur with or without clinician-specific variability and may be simplified for non-specialists' use. Additionally, the evaluation may occur at a patient database, or at a central database that is able to gather data from a user site, or any number of patient databases.

An example of the database evaluation is a determination of whether the specific parameter measured from the patient's swallowing profile falls within a normal range or is higher or lower than a normal range, and whether the ranges may be indicative of a swallowing dysfunction or disorder. This first evaluation results in a first evaluation output that is representative of, for example, a high or low reading, or a positive or negative indication of a swallowing dysfunction or disorder. The first evaluation output may be in a number of forms easily understood by the patient including, but not limited to, a print-out of the results of the evaluation, a blinking or color-coded light emitting diode ("LED"), an audible output, or any other electronic signal that may be representative of the first evaluation results.

For example, in an embodiment, the first evaluation results may be a print-out displaying ranges of normal quantitative or qualitative measurements for certain swallowing parameters, along with the patient's specific measurements for the same swallowing parameters. In this regard, the patient and/or health care provider will be able to easily determine what the normal ranges for the parameter are and whether the patient falls within those ranges, or is higher than or lower than the ranges.

After a first evaluation result is established, the processing device and/or a second processing device may further evaluate the first evaluation results. In an embodiment wherein the further evaluation occurs in a second processing device, the second processing device also cooperates with a patient database or a central database. After first results are further evaluated, the processing device outputs a second result(s), which is the product of the further (or second) evaluation. The form of the second result output may be the same as or different than the form of the first result output.

In an embodiment, the first evaluation result may be an electronic signal that may be sent to a different processor for further evaluation (e.g., a second evaluation). After the second evaluation, another output (e.g., a second evaluation result) may be output to the patient. For example, the first evaluation at a first processing device may result in a first evaluation result that is an electronic signal indicating the presence of dysphagia based on a swallowing pressure of a specific value. The first processor may transmit the value to a second processor for a second evaluation. In the second evaluation, the database may compare the electronic signal representative of a specific pressure value to known pressure ranges representative of certain types of dysphagic dysfunctions (e.g., mechanical, biomechanical, neurological, etc.), and output the specific type of dysfunction the patient is suffering from. The specific type of dysfunction, then, would be the second result and the product of the second evaluation.

In yet another embodiment, further evaluation can be performed using either first and/or second evaluation results, and yet another database that contains information related to therapy recommendations for specific swallowing dysfunctions. The database may include any known swallowing diseases and dysfunctions and correlate the diseases and dysfunctions with treatments that may be used to treat the disease/dysfunction and/or alleviate symptoms associated therewith. For example, in the previous embodiment, wherein the first result is an indication of dysphagia and the second result is a specific type of dysfunction, a third evaluation may take place at either of the first two processing units or at a third processing unit, wherein an electronic signal of the type of dysfunction is evaluated and compared to the therapy database to determine an optimum therapy regimen. Once the therapy or therapies are determined, the third output of a therapy recommendation may be output in a form that is easily understood by the patient and/or health care provider.

In an embodiment wherein therapy recommendations are provided, the therapy recommendation may be at least one of products, tools, or services tailored for the patient based on their diagnosed dysfunction/disorder. A recommended therapy plan may include, for example, at least two of physical therapy, occupational therapy, speech therapy, nutritional formulation, dietary modification, oral health improvement, electrical stimulation, biofeedback and pharmacological treatment. The dietary modification may include at least one of increased cohesiveness, increased thickness, trigeminal stimulants, swallowing stimulants, temperature modification of the food, texture modification of the food, and sensory modification of the food. Oral health improvement may include at least one of mouth wash, tooth paste, probiotics, saliva stimulants, toothbrush, dental floss, and tongue scraping. The skilled artisan will appreciate that the therapy recommendations are not limited to those disclosed herein and may include any known therapy for treating swallowing diseases or dysfunctions.

The skilled artisan will understand that the databases of the present disclosure can be updated. The updates may take place on a continuous basis or at predetermined times (e.g., quarterly or annually). The updates may take place by subscription and may be received via one of the internet, physical means, and over internet and physical means. The physical means may be at least one of a compact disc, DVD, flash drive, tape, or combinations thereof. Regardless of whether the database is a patient database located at or near the site of patient use, or a central database located at a remote location, all databases disclosed herein are capable of being updated.

As mentioned briefly above, a processing unit may output the first and/or second results in any manner that may be easily understood by a patient. For example, first, second, and third results may be displayed visually on a display of the processing unit 20 or second device 22, or via an illuminated light emitting diode ("LED"), etc. First, second, and third results may also be output via auditory means such as, for example, speakers, or via textured means such as, for example, Braille. The output may be one of an electronic signal; a diagnosis of disorder/dysfunction; at least one qualitative measure of the disorder/dysfunction; at least one quantitative measure of the disorder/dysfunction; a mechanical dysfunction; a biomechanical dysfunction; a neurological dysfunction; a qualitative or quantitative measure of a mechanical, biomechanical, or neurological dysfunction; a qualitative or quantitative measure of dysphagia; a swallowing impairment; a poor swallowing characteristic; an indication of poor lip sealing during swallowing; a classification of a swallowing dysfunction; a classification of a disorder; a classification of a dysphagia type; qualitative or quantitative measure of the classification of a swallowing dysfunction, classification of a disorder, or classification of a dysphagia type; a diagnosis of anatomic structures not functioning within normal parameters; a qualitative or quantitative measure of various parameters of one or more functions of one or more anatomical structure; and a risk of sequellae from disorder. In another embodiment, first, second, and third results may be in the form of a visible or audible question such as, for example, "does the patient have a disorder/dysfunction"?

In an embodiment, the first, second, and third result is the indication of a risk of sequellae from a disorder. The sequellae may be at least one of aspiration pneumonia, chronic obstructive pulmonary disorder ("COPD"), malnutrition, sarcopenia, dehydration, orthostatic hypotension, functional decline, falls, pressure ulcers, urinary tract infections, skin infection, conditions of specific nutrient deficiencies, choking, coughing, anxiety, and depression. When present, the sequellae may require at least one of emergency care, hospitalization, a visit to a doctor's office, medical treatment, and medication.

Using the combinations of sensors, databases and/or algorithms of the present disclosure provides for the diagnosis of various swallowing dysfunctions and disorders. In addition to the disorders and dysfunctions described above, the present disclosure also relates to any pathologies, syndromes, or diseases that can be diagnosed or classified using the measured parameters. For example, the disorders may also include at least one arthropathy, temporal mandibular dysfunction, colic, irritable bowel syndrome, irritable bowel disorder, at least one intestinal disorder, and at least one pathology, syndrome, disorder or disease that can manifest dysphagia.

In addition, providing the combination of sensors, databases and/or algorithms of the present disclosure also allows for early detection of various swallowing dysfunctions and disorders. Early detection provides for early treatment, which can provide for reduced medical care costs, reduced risk of dysfunctions and/or disorders, and reduced symptoms of existing dysfunctions and/or disorders. Health care costs may be reduced simply by reducing the patient's number of emergency room visits, hospitalizations, doctor's visits and/or medical treatments, depression, pain, anxiety, etc., and reduction in sequellae from dysphagia (e.g., COPD, aspiration pneumonia, malnutrition, etc.).

Early treatment can reduce the risk of conditions including, for example, malnutrition, dehydration, blocked airway, etc. It is important to reduce such conditions because they can lead to further health concerns. For example, malnutrition can lead to, among other things, suppression of the immune system of the patient, sarcopenia, dystonia of the muscles, and worsening of dysphagia. Dehydration can lead to, among other things, loss of appetite, fatigue or weakness, increased heart rate and respiration, increased body temperature, muscle cramps and nausea.

Devices 10 of the present disclosure may be manufactured using a hybrid integration to accomplish an optimum cost-performance trade off. Printed electronics are generally low-cost and use lower end elements. Printed electronics have long switching times, low integration density, large areas, flexible substrates, simple fabrication, and extremely low fabrication costs. In contrast, conventional electronics are generally higher-cost and use higher end elements. Conventional electronics have extremely short switching times, extremely high integration density, small areas, rigid substrates, sophisticated fabrication, and high fabrication costs. Devices 10 of the present disclosure, however, can use elements from both printed and conventional electronics to achieve an optimum cost-performance trade off. The hybrid integration of devices 10, for example, may use printed devices (sensors, batteries, conductive lines, etc.) for lower costs, as well as silicon devices (embedded computing) for high performance.

Devices 10 may be prepared using a roll-to-roll process, as is shown generally in FIG. 3. Roll-to-roll processing is the process of creating electronic devices on a roll of flexible plastic or metal foil. Roll-to-roll processing is similar to the process used for newspaper printing and is still a developing technology that could prove very useful in the future for fabricating many devices at a fraction of the cost of traditional semiconductor manufacturing methods.

An important advantage of the apparatuses and methods of the present disclosure is that the system will link the measurements obtained by the sensors to an underlying swallowing dysfunction (a biomechanical fault), and not to an underlying disease, which has probably already been diagnosed by a healthcare professional. As a result, the underlying biomechanical fault may be evaluated and treated, which can, in turn, reduce a patient's symptoms of dysphagia and aspiration. In this regard, knowledge of the biomechanical fault will allow for more efficient treatment of dysphagia and aspiration through recommended use of specific products, tools and services whose properties are linked to the specific diagnosed mechanical dysfunction. In an embodiment, devices 10 can be manufactured to be integrated and disposable, and are convenient, easy to use, and provide rapid results.

The skilled artisan will appreciate that devices 10 of the present disclosure are not limited to the methods and uses described herein. Instead, devices 10 may be used in any application wherein use of devices 10 is beneficial. Other applications include, for example, intelligent packaging, low-cost radio frequency identification ("RFID") transponders, rollable displays, flexible solar cells, disposable diagnostic devices, printed batteries, wearable devices/smart textiles, and various other sensor applications. For example, the present technology may be used to manufacture smart RFID sensing tags in plastic foil that act as sensors, use a thin film battery and use printed electronics for communication. Additionally, devices 10 of the present disclosure may be used as multi-sensor platforms on plastic foil, wherein the sensors act as, for example, a capacitive volatile organic compound sensor, a resistive temperature sensors, a capacitive humidity sensor, etc.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating a patient with a swallowing dysfunction, the method comprising:
    measuring a swallowing profile of the patient using a sensor, the sensor comprising a flexible substrate, and at least one printed electronic selected from the group consisting of a microcontroller, at least one sensor, an antenna, and combinations thereof, wherein the flexible substrate and at least one printed electronic are encased in a plastic foil;
    sending a sensor output to a device having a processor and a swallowing profile database, wherein the swallowing profile database comprises data relating to both healthy patients and patients having swallowing dysfunctions, wherein the data relating to healthy patients is recorded using two methods: i) recording truly healthy data during an initial measurement using a videofloroscope; and ii) recording composite healthy data during a second measurement, the composite healthy data reflecting a first function of a neck of the patient, the neck having an apparent dysfunction of the patient and a second function of a lip seal of the patient that is functioning as per a normal individual;
    comparing the sensor output with the data of the swallowing profile database relating to both healthy patients and patients having swallowing dysfunctions, linking the sensor output to an underlying swallowing dysfunction without linking the sensor output to an underlying disease, to obtain a first signal output indicative of a range of a swallowing dysfunction;
    comparing the first signal output to a recommended therapy database to obtain a second signal output representative of a therapy recommendation comprising at least two of: physical therapy, dietary modification, oral health improvement, electrical stimulation, biofeedback, and pharmacological treatment; and
    treating the patient in accordance with the second signal output by administering an effective amount of the therapy recommendation to the patient.

2. The method according to claim 1, wherein the first signal output is an electronic signal.

3. The method according to claim 1, wherein the data is obtained from measurements made with videofluoroscopy tests for at least 500 patients comprising healthy patients and dysphagic patients.

4. The method according to claim 1, wherein the underlying swallowing dysfunction is a biomechanical fault.

5. The method of claim 1, wherein the database is a remote database located remote from the sensor.

* * * * *